United States Patent [19]

Shutt

[11] Patent Number: 5,141,517
[45] Date of Patent: Aug. 25, 1992

[54] RETRACTABLE INSTRUMENT
[75] Inventor: George V. Shutt, Glendora, Calif.
[73] Assignee: Zimmer Inc., Warsaw, Ind.
[21] Appl. No.: 465,673
[22] Filed: Jan. 16, 1990
[51] Int. Cl.⁵ .......................................... A61B 17/32
[52] U.S. Cl. .................................. 606/167; 606/170;
606/172; 604/36; 30/162; 30/335; 30/342
[58] Field of Search ............... 606/172, 167, 170, 159;
604/36, 110, 181; 30/162, 335, 340, 342;
401/82, 99, 258

[56] References Cited
U.S. PATENT DOCUMENTS

| | | |
|---|---|---|
| 174,417 | 3/1876 | Evans . |
| 715,646 | 12/1902 | Driscoll . |
| 1,339,692 | 5/1920 | Diamant . |
| 1,449,408 | 3/1923 | Hull . |
| 1,482,300 | 1/1924 | Hansen .................. 401/82 |
| 1,701,771 | 2/1929 | Di Stefano .............. 401/99 X |
| 2,131,780 | 10/1938 | Storz . |
| 2,258,287 | 10/1941 | Grieshaber . |
| 2,427,068 | 9/1947 | Randolph ............... 401/99 X |
| 2,517,158 | 8/1950 | Ahmer . |
| 2,843,128 | 7/1958 | Storz . |
| 3,835,859 | 9/1974 | Roberts et al. . |
| 4,067,340 | 1/1978 | Le Noir . |
| 4,281,458 | 8/1981 | Okada . |
| 4,444,184 | 4/1984 | Oretorp . |
| 4,491,132 | 1/1985 | Aikins . |
| 4,500,221 | 2/1985 | Emerson ................. 401/82 |
| 4,674,500 | 6/1987 | De Satnick . |
| 4,963,048 | 10/1990 | Thomas et al. ........... 401/99 X |

Primary Examiner—Robert Bahr
Assistant Examiner—J. Doyle
Attorney, Agent, or Firm—Gene Warzecha

[57] ABSTRACT

A retractable surgical or other instrument is provided with a locking mechanism automatically actuated by sliding an operating element forward to extend it from a protective sheath. The locking mechanism operates by the cooperative action of a plurality of abutment means integrally molded into the interior of the instrument handle and a plurality of transverse bends forming a substantially closed loop profile in the proximal end of the elongated support shaft of the operating element. A longitudinally slidable actuating pin engages the proximal end of the support shaft to move it longitudinally in a selected direction. A portion of the proximal end of the shaft is biased to exert a radially outward force on the inner wall of the instrument handle thereby assuring positive engagement between the support shaft and an abutment surface which prevents rearward motion of the surgical element once it is placed in an extended position. Additional abutment surfaces are provided to enhance the locking effect and additional bends are provided in the proximal end of the support shaft to enable the slide switch to overcome the radially outward bias in order to retract the surgical element when desired.

30 Claims, 4 Drawing Sheets

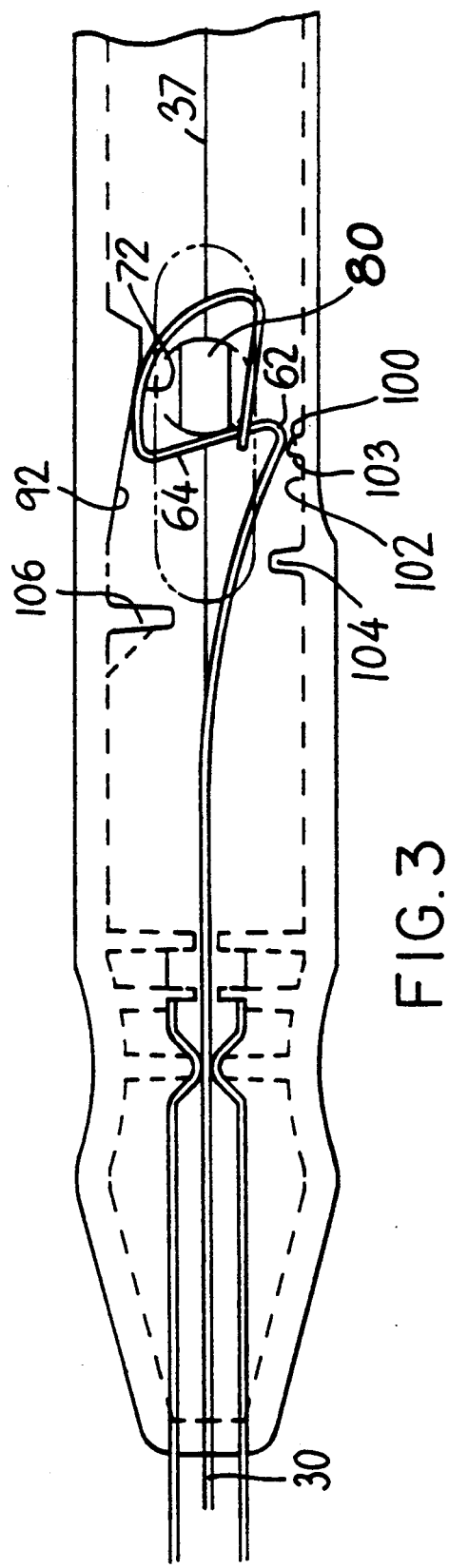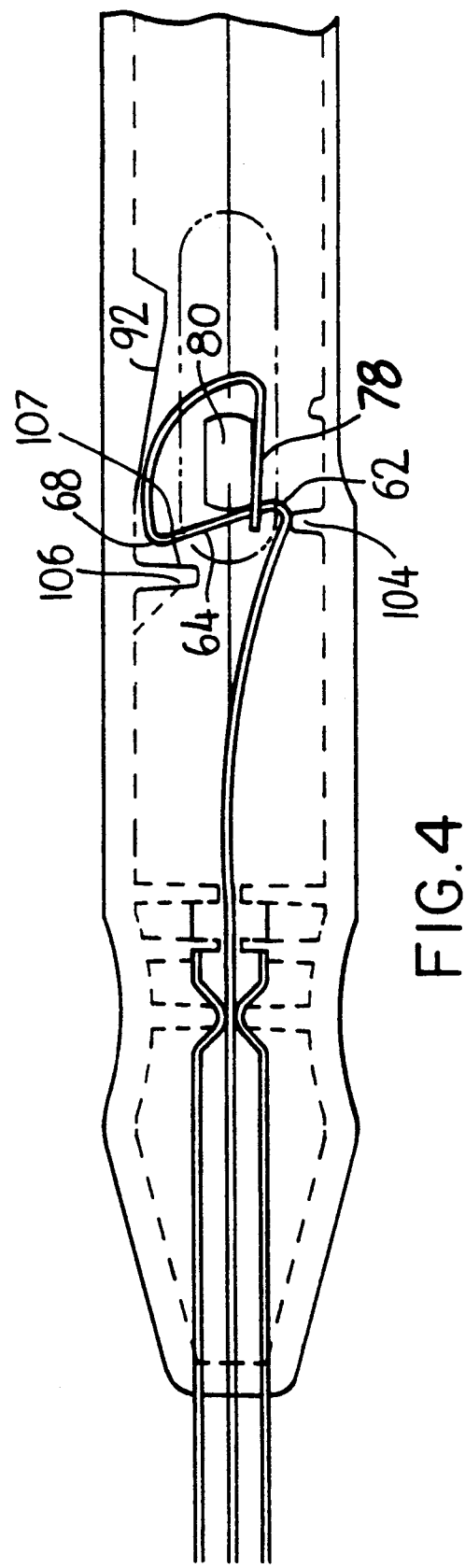

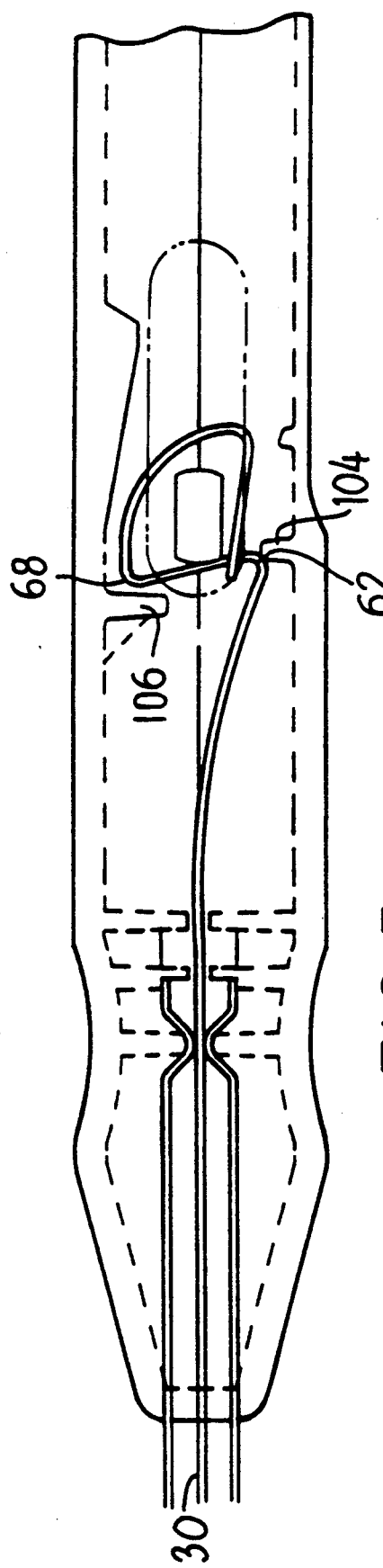
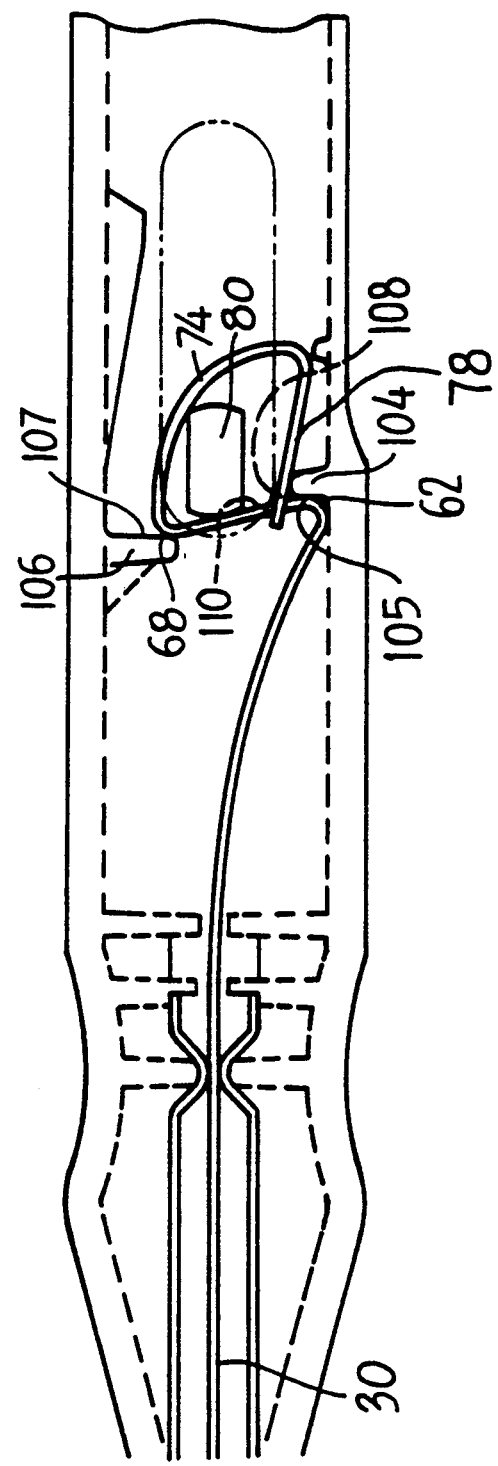
FIG.5
FIG.6

RETRACTABLE INSTRUMENT

BACKGROUND OF THE INVENTION

1. Field of the Invention

The invention relates generally to retractable devices which have an operating element movable between an exposed, working position and a covered, storage position More particularly, the invention relates to retractable, surgical devices which have an operating element lockable in a plurality of selected cutting positions. Still more particularly, the invention relates to disposable, retractable surgical cutting devices.

2. Description of the Prior Art

Retractable cutting devices for use in surgical procedures are commonly known in the prior art. The retractable nature of such devices assures that the cutting surface will be held retracted within the device in such a way as to not interfere with the placement of the device adjacent the area to be operated upon, whereupon the cutting surface may be extended in order to perform the desired surgical procedure without injuring surrounding tissue.

The present invention is particularly adaptable to small cutting instruments and is, therefore, intended primarily for use in arthroscopy or microsurgery of the knee and other joints in humans (or other animals). It will be understood, however, that the principles of this invention are equally applicable to other surgical, and even non-surgical cutting and non-cutting devices For these reasons, the use herein of the terms "knife", "cutting", "blades" and the like should not be considered as limiting the scope of the invention.

Arthroscopy involves the use of viewing, probing and cutting devices that can be utilized through a very small opening in the patient's skin. The procedure necessarily involves the steps of insertion, retraction and manipulation of various devices through the skin to an area to be operated upon. Such steps are primarily blind until the device comes into view of the arthroscope. Consequently, it is desirable that any cutting or other potentially dangerous instruments be protected from either unintentionally injuring the patient or from being damaged by other tools during the blind maneuvers. Retractable cutting devices are obviously quite desirable in arthroscopic procedures.

Prior art arthroscopic cutting devices are generally available in either one of two configurations: (1) a separate sheath configuration having an unsheathed and unprotected disposable operating member (e.g. knife blade) situated on long, reusable handles and intended to be inserted within tubular sheaths previously placed separately through the skin, or (2) a combination configuration having a disposable sheathed blade which is retractable within a sheath on a permanent handle, the sheath being inserted through the skin simultaneously with the knife. The separate sheath system is cumbersome to use and almost always has a dulling effect on the cutting surfaces of the operating member as they rub the inner wall of the sheath. The combination configuration is a safer system, although it still has several undesirable characteristics. The permanent handle is very costly, and, therefore, usually only one handle is available. This requires the surgeon to decide which operating member or cutting blade (out of possibly 20 or so typical configurations) should be placed in the handle before surgery. Alternatively, the surgeon must wait until the surgical procedure has begun in order to decide which blade to use, whereupon the blade must be removed from its sterile packaging and assembled into the handle. This procedure obviously affects the surgeon's efficiency and concentration. Additionally, the procedure inhibits the surgeon from using a variety of blades which may otherwise be the most optimal configuration for u se during various portions of the procedure. Once the sterile package is opened and a blade is inserted into the handle, the surgeon will tend to complete the procedure using this first blade rather than waiting to have a (possibly more appropriate) blade or other device inserted into the handle.

The prior art disposable blade/permanent handle system incorporates a locking method to lock the knife blade relative to the handle in an extended position during surgery. Prior art locking mechanisms are cumbersome and require more than one motion to affect any movement of the blade relative to its housing. One type of locking device, shown for example in U.S. Pat. No. 4,674,500 (DeSatnick), requires the surgeon to push a slide mechanism longitudinally forward and rotate it laterally relative to the handle in order to lock the slide mechanism into a detent Such a mechanism is awkward to use and has been found to be susceptible to accidental unlocking. The design also necessarily introduces "play" or uncontrolled movement in the blades, which movement must be dampened by deliberately bending the blades (or their support shafts) to cause a binding interference fit within the sheath attached to the handle. This results in a very rough actuation and retraction of the blade. Another type of prior art locking device, shown for example in U.S. Pat. No. 4,491,132 (Aikens), requires the surgeon to transversely deflect a locking pin to enable a blade to be slid longitudinally to place the locking pin into engagement with a selected detent in the handle. This mechanism is also difficult to use.

Additionally, the prior art disposable blade/permanent handle devices may tempt people to reuse already used blades. Even though the blades may have been sterilized prior to reuse, this is a risky procedure, not only because the blades may not be sterilized well enough, but because the blades may not be sharp enough for subsequent uses, thereby affecting the surgical procedure to be performed on subsequent patients.

In order to overcome the foregoing disadvantages, it is an object of this invention to provide a retractable surgical instrument which is disposable.

It is a further object of this invention to provide a retractable surgical instrument having a handle and an operating or cutting element, the entire device including the handle assembly being disposable.

It is an additional object of this invention to produce a high quality retractable arthroscopic knife which is relatively inexpensive and disposable.

It is still another object of this invention to provide a retractable, sheathed surgical instrument having an improved locking mechanism enabling the active, operating element of the instrument to be locked into a plurality of extended positions relative to a housing or sheath.

It is still another object of this invention t provide a retractable instrument having a locking mechanism which is automatically actuated by a single manual motion of the user and which is not easily disengaged during use. It is a further object to disclose a method for achieving these purposes in a retractable surgical instrument.

It is an additional object of this invention to provide a retractable surgical instrument wherein the actual operating element or cutting surface, a covering sheath and the instrument handle are integrally formed in one nondisassemblable unit.

SUMMARY OF THE INVENTION

These and other objects of the invention are achieved by the preferred embodiment disclosed herein which is a retractable surgical instrument comprising: a housing; a longitudinally movable support shaft having a proximal end thereof situated within said housing, said proximal end having a substantially planar, generally closed-loop profile in a first axial plane, said profile having at least one rearwardly projecting abutment point adapted to prevent rearward longitudinal motion of said support shaft upon engagement of said point with an abutment surface; means for biasing said abutment point in a direction transverse to said longitudinal direction; an operative surgical element secured to the distal end of said support shaft and movable therewith between a retracted position, wherein said surgical element is enclosed by said housing, and at least one extended position, wherein said surgical element is extended from said housing; slide means accessible from the exterior of said housing and longitudinally slidable along the axis of said support shaft, said slide means having an actuating pin projecting into said housing a predetermined distance sufficient to cause said pin to project into the plane of said substantially closed loop, said pin being movable in a second axial plane transverse to said first axial plane, whereby longitudinal motion of said pin will effect longitudinal motion of said proximal end; an abutment surface projecting into the normal path of said abutment point and automatically engaged by same upon a predetermined amount of forward longitudinal motion thereof to prevent rearward motion of said surgical element from a selected one of said extended positions.

In the preferred embodiment, the support shaft profile is formed to include an advancing section, for advancing the surgical element from the housing, and a retracting section for overcoming the transverse bias of the abutment point to enable the element to be retracted by simple rearward longitudinal motion of the slide.

BRIEF DESCRIPTION OF THE DRAWINGS

FIG. 3 is a view of the actuating mechanism shown in FIG. 2 when the operating element is in a partially extended position.

FIG. 4 is a view of the actuating mechanism shown in FIG. 3 in a further extended position.

FIG. 5 is a view of the actuating mechanism shown in FIG. 4 in a position just prior to locking the operating element in a fully extended position.

FIG. 6 is a view of the actuating mechanism shown in FIG. 5 when the operating element is in a fully extended and locked position.

DESCRIPTION OF THE PREFERRED EMBODIMENT

Figure 1:
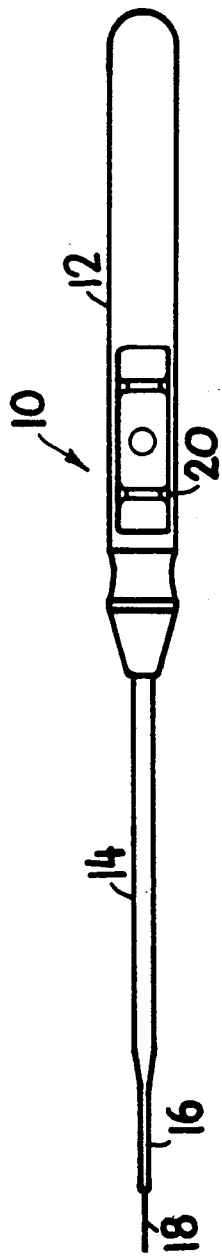
FIG. 1 is a top plan view of an arthroscopic instrument constructed in accordance with the principles of this invention.
Figure 2:
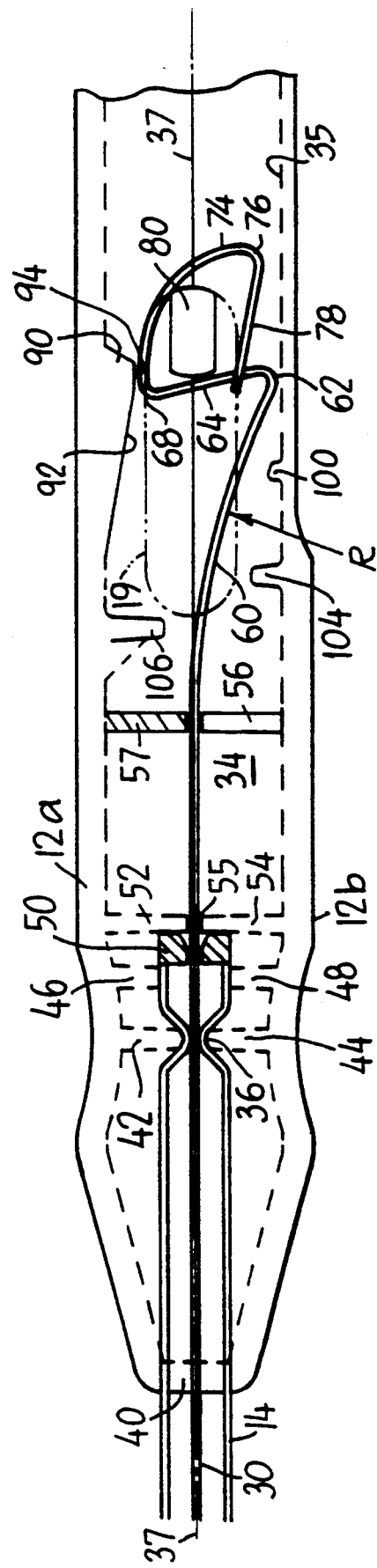
FIG. 2 is a cut-away view of a portion of FIG. 1 showing the internal construction of the instrument and showing the actuating mechanism of the instrument when the operating element is in a fully retracted position.

Referring to the drawings, there is shown a diagrammatic plan view of an arthroscopic sheathed instrument 10 constructed in accordance with the principles of this invention Instrument 10 comprises a cylindrical handle 12, a tubular extension member 14 attached to one end of the handle and ending at its distal end in an integrally formed, flattened sheath 16, an operating element or cutting device 18 and a longitudinally movable slide trigger 20 for extending and retracting cutting device 18 relative to sheath 16. It will be understood that cutting device 18 may have a variety of cutting edges and need not be shaped like a conventional knife blade. Indeed, cutting device 18 is meant herein to encompass even non-cutting operating elements such as hooks, probes, forceps, scissors, punches, etc.

Referring now to FIGS. 2 through 6, the construction and method of operation of the extension/retraction actuating means of the invention will be described. Trigger 20 has a pin 80 extending into the interior of handle 12, the pin being slidable within slot 19 shown in phantom. The trigger is aligned within slot 19 by an inner flange (not shown) to prevent lateral motion. Cutting device 18 is integrally formed with a longitudinally extending support shaft or extension 30 axially situated within tube 14 and extending therethrough into interior chamber 34 of handle 12. Handle 12 may be formed of any suitable material and, in the preferred embodiment, is formed from two complementary halves 12a and 12b of a molded high-impact styrene ultrasonically welded together. Tube 14 is held aligned along handle axis 37 by the cooperative action of front aperture 40, inwardly extending intermediate projections or walls 42 and 44 and inwardly extending rear-end projections or walls 46 and 48. Projections 42 and 44 serve as stops to limit axial forward and rearward longitudinal motion of tube 14 by extending into the handle interior a sufficient distance to hold pre-crimped tube 14 at point 36 near its proximal end. The rear end of tube 14 presses against seal 50 retained between projecting walls 46 and 48 and projecting walls 52 and 54 to prevent any fluid at the operating site from flowing past. Walls 52 and 54 meet to form a slit (or other complementarily shaped opening) 55.

Shaft 30 is formed from a high quality, stainless spring steel capable of having its proximal end preformed into a predetermined profile to serve as an actuating portion comprising a plurality of bends, of varying degrees, and straight sections of varying lengths. The actuating portion of shaft 30 is formed as generally closed planar loop which cooperates with various other structures described below to produce an actuating means for extending, retracting and locking cutting device 18 at various longitudinal positions relative to sheath 16.

In the preferred embodiment, slide trigger 20 is longitudinally slidable on handle 12 within a first axial plane and, by means of projecting pin 80, trigger 20 is able to engage the loop formed in the proximal end of shaft 30 by virtue of the latter having a predetermined planar profile in a second axial plane transverse to that of the sliding projecting pin. Trigger slot 19 prevents excessive force from being applied to the proximal end of the shaft to avoid deforming same and possibly causing improper operation of the device.

Shaft 30 passes through window 56 in wall 57 and has a biasing arc 60 of large radius R formed between a portion of the shaft on axis 37 and an acute, forwardly directed bend 62. Window 56 is wide enough and high enough to limit lateral motion of shaft 30 while enabling longitudinal motion. Arc 60 causes shaft 30 to be outwardly biased against inner wall 35 of chamber 34 and causes bend 62 to apply a spring pressure radially outwardly from axis 37 at the point where the most radially outward side of bend 62 touches inner wall 35. It will be understood below that, while bend 62 is longitudinally slidable within handle 12, the interaction of bend 62 with projections inwardly extending into chamber 34 creates a positive lock against rearward axial motion of shaft 30. The preferred embodiment disclosed herein includes a handle 12 and tube 14 having a circular cross-section and the profile of the actuating spring portion of shaft 30 is aligned in an axial plane in order to clarify that the various bends formed in the actuating portion are transverse to the handle and shaft axes (which are identical in the preferred embodiment). Consequently, reference is occasionally made herein to various forces or components being "radially" directed. This terminology is used only for explanatory purposes and should not be construed as limiting. While it is necessary that some forces be directionally biased relative to axis 37, it will be understood that the invention could be embodied in other than a circular cross-section form.

While shaft 30 may be of any desired cross-section, it has been found that if shaft 30 is flat (i.e. shown in edgewise in FIGS. 2-6 and in plan view in FIG. 7), then the interaction of the broad, flat surfaces of shaft 30 with crimp 36 as well as other surfaces within the interior of handle 12 will enhance the ability of shaft 30 to resist rotation about axis 37. For explanatory purposes, it will be understood that shaft 30 is formed from a flat spring material and each of the various bends referred to herein is made in a plane transverse to the plane of the flat shaft body and transverse to the longitudinal axis 37 of shaft 30.

Bend 62 produces a upwardly (and longitudinally forwardly) extending, straight, spring portion 64 extending diametrically away from inner wall 35 for predetermined distance which, in the preferred embodiment, is greater than one-half the diameter of chamber 34. Spring portion 64 may be deemed to serve as an engaging/advancing section, as will be understood below. While portion 64 is described as extending "longitudinally forwardly", it should be clear that this is not an axially aligned direction and that portion 64 is oblique to the axis. At the other end of portion 64, a rearwardly directed bend 68 is formed into shaft 30 to create a rearwardly extending, arcuate spring portion 74. At the end of portion 74 a final, forwardly directed bend 76 is made to create a forwardly extending tail portion 78 of shaft 30. Spring portion 74 may be deemed to serve as a disengaging/retracting section, as will be understood below.

Inwardly extending actuating pin 80 is axially situated between portions 64 and 74 of shaft 30. Longitudinal motion of pin 80 against portion 64 will cause shaft 30 to advance and lock, and longitudinal motion of pin 80 against portion 74 will cause shaft 30 to unlock and retract.

As trigger means 20 and its associated actuating pin 80 are moved forward, actuating pin 80 contacts the rearwardly facing side of engaging/advancing spring section 64 urging it longitudinally forward until the forwardly facing side of arc 60 contacts the rearward side of inwardly extending first projection 100. As shaft 30 continues its forward motion, bend 62 will ride up and over projection 100. Portion 64 has a forward tilt in order to bias bend 62 against wall 35 during forward motion of shaft 30. This causes bend 62 to positively snap over projection 100 while also causing bend 62 to fall wa from pin 80. A non-tilted section 64 would not provide the same feel. When bend 62 snaps over the forward side of projection 100 it will be radially outwardly biased against inner wall portion 102 immediately forward of projection 100. The longitudinal abutting engagement between acute bend 62 and the forwardly facing abutment surface 103 of projection 100 provides a positive lock against rearward motion of shaft 30. While bend 62 is used in the preferred embodiment as an abutment point, those skilled in the art will understand that a comparable abutment point may be created in other ways.

Further forward motion of pin 80 urges engaging/advancing spring section 64 longitudinally forward until bend 62 is pushed up and over second projection 104 as best seen in FIGS. 4 and 5. It will be noted that the distance between the radially most inward part of projection 104 and the diametrically opposed section of chamber 34 (including the bottom of ramp 92) must be such as to enable straight section 64 to pass through this gap. A third radially inwardly directed projection 106 is diametrically opposed to projection 104 and a predetermined distance forward thereof in order to assure that it enables sufficient forward motion of bend 68 so as not to interfere with the ability of bend 62 to snap over projection 104. Furthermore, as will be best seen in FIG. 6 showing a fully extended and locked position, projection 106 must extend radially inwardly a sufficient distance in order to enable the rearwardly facing abutment surface 107 of projection 106 to contact bend 68 while bend 62 is in contact with the forwardly facing abutment surface 105 of projection 104. In this position both forward and rearward motion of shaft 30 is minimized.

It should be understood that inwardly extending projections 100, 104 and 106 are shaped to operate properly in conjunction with the particular shape of shaft 30. In the preferred embodiment, because shaft 30 is flat, these projections extend transversely as shown.

Inner wall 35 is provided with a radially inwardly extending biasing projection 90 having a ramp surface 92 terminating in a longitudinally extending ledge 94 situated a predetermined distance from axis 37. Ramp 92 and ledge 94 are sized in order to assist in the retraction of shaft 30. It will be understood by those skilled in the art that under certain circumstances the cutting element may encounter resistance which would prevent easy retraction into the housing. In such a situation, the continued rearward motion of pin 80 would cause it to contact the inner arcuate surface of bend 74 adjacent the least inclined portion thereof near bend 76. Ramp, 92 causes arcuate portion 74 to move downwardly as viewed in FIG. 2 in order to engage the pin at a more greatly curved portion of section 74. The radially outward bias of the proximal end of the shaft thereby assists in retracting the blade.

Figure 7:
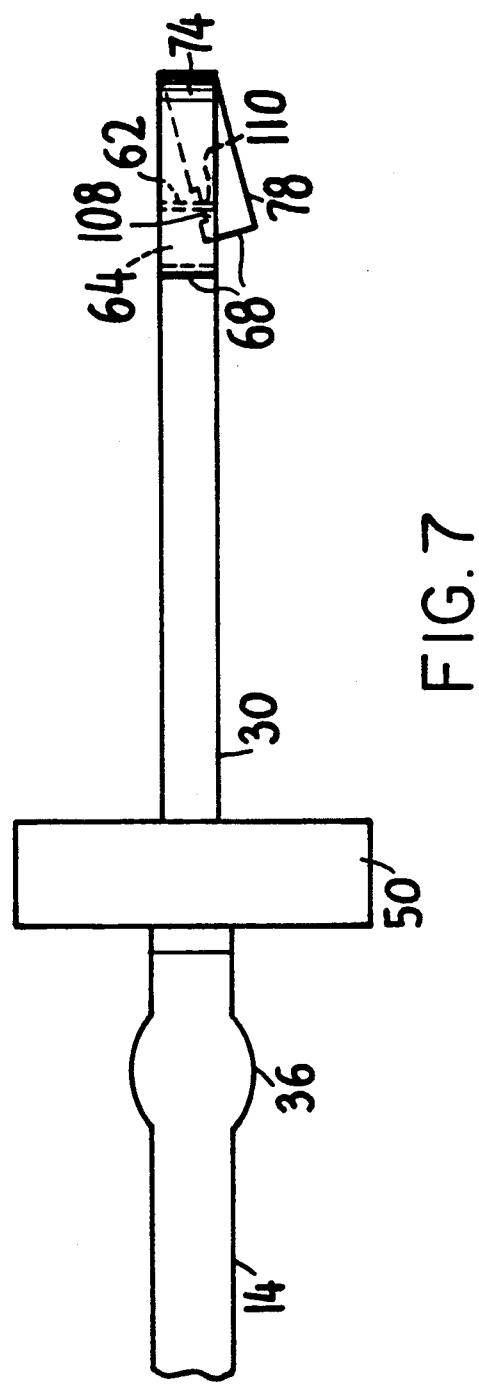
FIG. 7 is a plan view of a portion of FIG. 6.

FIG. 7 is a top plan view of the proximal end of shaft 30. Tail end 78 of shaft 30 has a notch 108 adapted to engage with a cooperating notch 110 formed in portion 64. The natural tension between end portion 78 and portion 64 keeps the notches pressed toward each other and the interaction of the notches assists in maintaining the closed-loop shape of the proximal end of shaft 30.

The preferred embodiment utilizes two projections (100 and 104) in order to provide a two-position locking mechanism. It will be understood that any number of such projections may be used depending upon the desired number of locked positions desired. However, the various projections should be of differing heights if their longitudinal spacing requires this to avoid interference, and ramp 92 should be sloped accordingly if the longitudinal travel of pin 80 is changed.

It will be apparent to those skilled in the art that, depending on the particular surgical procedure involved, cutting device 18 may be subjected to longitudinal forces in either direction relative to the handle 37 axis. The locking means of the invention is uniquely capable of resisting these natural forces sufficiently to prevent cutting device 18 and its associated support shaft 30 from being either removed from or pushed into handle 12. It will be noted that the cooperative action between the abutment surfaces of inwardly projecting members 104 and 106 in cooperation with the unique profile of the shaft achieves the desired functions. In particular, it will noted that any force tending to push cutting device 18 to the right (as viewed in FIG. 6), that is into the handle, will be resisted by the primary abutting contact between bend 62 and the forwardly facing abutment surface 105 of projection 104. Any force tending to pull cutting device 18 to the left (out of the handle) will be resisted by the secondary abutting contact between the rearwardly facing abutment surface 107 of projection 106 and bend 68 and will be additionally resisted by an increased radially outwardly directed force on bend 62 created by the rotation of section 64 about bend 62, the rotation being created by the abutting contact at bend 68.

While the foregoing has described the various components of the actuating spring portion of the invention and their operation during the advancement of the support shaft 30 and its associated operating element 18 from handle 12, the invention is also capable of automatically retracting the shaft and the operating element in response to a simple rearward longitudinal motion of slide 20. Referring to FIG. 6, where the actuating spring portion is shown in a fully extended position, when one desires to retract the operating element from its fully extended position slide 20 and pin 80 are longitudinally slid rearwardly (to the right as shown in FIG. 6) which causes the rearwardly facing side of pin 80 to contact the curved forwardly facing side of disengaging/retracting spring section 74. Continued rearward motion of pin 80 causes section 74 to pull bend 68 primarily upwardly because of the arcuate sloping profile of section 74 in the area contacted by the pin. Upward motion of bend 68 necessarily overcomes the bias of arc 60 and causes upward motion of bend 62 so that it may clear projection 104 (or 100). Continued rearward motion of pin 80 causes the pin to push primarily rearwardly by contacting a less sloped area of section 74 (less inclined relative to the axis) to produce less "lift" and more retractive force.

While the preferred embodiment has been described in terms of a unitary operating element and sheath, the rear end of which is formed into a particular planar shape it will be understood that various geometrical configurations of the proximal end of shaft 30 may be suitable. Similarly, other internal structures may be utilized within the handle. For example, the loop formed in the proximal end of the shaft need not be totally closed provided that a portion of the shaft is bent to be engageable by an actuating pin in order to advance the mechanism into locking engagement with an abutment surface, and further provided that another portion of the shaft is bent to provide a retracting mechanism, etc. A split pin could possibly be used to engage one shaft portion to perform both advancing and retracting functions. The abutment projections shown in the preferred embodiment may be replaced by stepped interior chamber of the handle so that the ledges formed by the various steps may serve as abutment surfaces. Additionally, while the preferred embodiment shows the proximal end of the shaft by means of a preformed arcuate bend, other arrangements may be suitable where the shaft is not preformed with an outward bias but is formed as a straight line terminating at some abutment point, the body of the shaft then being biased outwardly to enable the shaft to move past the abutment point. Other configurations of the invention may be made with the operational parts of the proximal end of the support shaft being biased in a direction other than the radially outward bias disclosed herein. Furthermore, while the preferred embodiment is shown to be longitudinally operated, the principles of the method and apparatus disclosed could be adapted to a rotary trigger motion.

It will be understood by those skilled in the art that numerous other modifications and improvements may be made to the preferred embodiment of the invention disclosed herein without departing from the spirit and scope thereof.

What is claimed is:

1. A retractable instrument comprising:
   a handle;
   an elongated tubular member secured to and extending from said handle;
   an elongated, longitudinally movable support shaft aligned within said tubular member, said support shaft having a proximal end thereof extending rearwardly of said tubular member into said handle, said proximal end bent into a predetermined profile;
   an operative element secured to the distal end of said support shaft and movable therewith between a retracted position, wherein said element is enclosed within said tubular member, and at least one extended position, wherein said element is extended from said tubular member;
   trigger means operatively situated on said handle for extending and retracting said element, said trigger means comprising an actuating pin adapted to engage a predetermined portion of said profile to thereby move said element between said retracted and extended positions;
   locking means responsive to a predetermined forward motion of said actuating pin for automatically locking said element in an extended position relative to said tubular member.

2. A retractable instrument according to claim 1 further comprising:
   a retracting means responsive to rearward motion of said actuating pin for unlocking and retracting said element from one of said extended positions.

3. A retractable instrument according to claim wherein said trigger means is adapted to be longitudinally slidable along the exterior of said handle.

4. A retractable instrument according to claim 1 wherein said predetermined profile comprises a substantially closed loop.

5. A retractable instrument according to claim 4 wherein said loop is planar and said actuating pin extends transversely through the plane of said loop.

6. A retractable instrument according to claim 1 wherein said element is flat and further comprising:
an elongated, generally flat sheath secured to the distal end of said tubular member, said sheath open at its distal end and adapted to receive said flat element in a retracted position.

7. A retractable instrument according to claim 1 wherein said locking means comprises:
a means for biasing said proximal end of said support shaft radially outwardly relative to the axis thereof;
a first abutment point on said support shaft adjacent said proximal end, said bias of said proximal end causing said first abutment point to be biased radially outwardly against the inner wall of said handle; and
a first abutment surface means extending a first predetermined distance inwardly from the inner wall of said handle to abut the rear side of said first abutment point and thereby prevent rearward motion of said element from an extended position.

8. A retractable instrument according to claim 7 wherein said biasing means comprises first arcuate transverse bend formed into said support shaft adjacent said proximal end thereof.

9. A retractable instrument according to claim 7 wherein said predetermined profile comprises:
means for sliding said first abutment point longitudinally forwardly from a position rearwardly of said first abutment surface means until said first abutment point on said support shaft slides forwardly over said first abutment surface means and into engagement therewith.

10. A retractable instrument according to claim 9 wherein said means for sliding comprises a first profile portion of said predetermined profile substantially transverse to the axis of said support shaft, said first profile portion adapted to be engaged by said actuating pin upon forward longitudinal motion thereof to slide said first abutment point forwardly.

11. A retractable instrument according to claim 2 wherein said locking means comprises:
a means for biasing said proximal end of said support shaft radially outwardly relative to the axis thereof;
a first abutment point on said support shaft adjacent said proximal end, said bias of said proximal end causing said first abutment point to be biased radially outwardly against the inner wall of said handle; and
a first abutment surface means extending a first predetermined distance inwardly from the inner wall of said handle to abut the rear side of said first abutment point and thereby prevent rearward motion of said element from an extended position and wherein said retracting means comprises:
means for overcoming the radially outwardly directed bias of said first abutment point in order to enable rearward longitudinal motion thereof past said first abutment surface means.

12. A retractable instrument according to claim 11 wherein said overcoming means comprises:
a second profile portion of said predetermined profile having a predetermined arcuate surface adapted to be engaged by said actuating pin upon longitudinally rearward motion thereof and adapted to move said first abutment point radially inwardly and to pull same rearwardly over and past said first abutment surface means.

13. A retractable instrument according to claim 7 wherein said locking means further comprises:
a second abutment point on said support shaft, said second abutment point situated longitudinally forward of said first abutment point;
a second abutment surface means situated longitudinally forward of said first abutment surface means and extending inwardly from the inner wall of said handle to abut the forward side of said second abutment point and thereby prevent forward motion of said element when said first abutment point abuts said first abutment surface means.

14. A retractable instrument according to claim 13 wherein said first and second abutment points lie in the same plane and wherein said second abutment surface means is situated at a point substantially diametrically opposed to said first abutment surface means.

15. A retractable instrument according to claim 13 wherein said retractable element and said support shaft are integrally formed.

16. A retractable instrument according to claim 2 wherein said predetermined profile lies in a first axial plane and wherein said actuating pin is movable in a second axial plane transverse to said first axial plane.

17. A retractable instrument according to claim 16 wherein said predetermined profile of the proximal end of said support shaft cooperates with portions of said handle, said predetermined profile comprising:
a first, arcuate portion extending rearwardly from a first point on the axis of said support shaft to a first bend contiguous to the inner wall of said handle;
a second, straight portion extending at a predetermined angle longitudinally forwardly from said first bend to a second rearwardly directed bend;
a third, arcuate portion extending rearwardly from said second bend; and
said portions of said handle comprising:
a first abutment surface extending into the interior of said handle at a first predetermined point situated rearwardly of the proximal end of said tubular member, said first abutment surface adapted to engage said first bend to prevent rearward motion thereof.

18. A retractable instrument according to claim 17 further comprising:
a second abutment surface extending into the interior of said handle at a second predetermined point situated substantially diametrically opposite from, and longitudinally forwardly of said first predetermined point, said second abutment surface adapted to engage said second bend to prevent forward motion thereof when said first abutment surface is in engagement with said first bend.

19. A retractable instrument according to claim 1 further comprising:
a fourth, straight portion extending forwardly from the end of said third portion to a free, terminal end of said support shaft.

20. A retractable instrument according to claim 19 further comprising:
said terminal end of said support shaft lying adjacent said second portion and having a notch therein adapted to receive a part of said second portion.

21. A retractable instrument according to claim 1 wherein said tubular member, said handle, said trigger means, said support shaft and said element are secured together as non-disassemblable, disposable unit.

22. A retractable instrument according to claim 6 wherein said support shaft is flat and wherein said tubular member has a crimped portion adjacent its proximal end and wherein said crimped portion further comprises diametrically opposed points on the wall of said tubular member which are pushed inwardly toward each other to decrease the distance therebetween to provide axial support for said support shaft.

23. A retractable instrument according to claim 17 further comprising:
an inwardly extending ramp projection formed on the interior of said handle opposite said first abutment surface, said ramp projection having a ramp surface extending from a first position proximate the inner wall of said handle to a second position spaced a predetermined distance inwardly therefrom, said second position situated rearwardly of said first position, said ramp surface adapted to urge said second portion radially away therefrom.

24. An advancing/retracting actuating means for a surgical instrument having a housing and an operating member longitudinally retractable into and extendable from said housing, said actuating means activated by a manually operable, longitudinally movable slide and capable of locking said operating member in a selected extended position relative to said housing and capable of retracting same from said extended position, said actuating means comprising in combination:
an axially slidable support shaft secured to the proximal end of said operating member comprising:
a first, arcuate portion extending rearwardly from a first point on the axis of said support shaft to a first bend contiguous to the inner wall of said housing;
a second, straight portion extending at a predetermined angle from said first bend in a generally longitudinally forward direction to a second bend, said second, straight portion extending in an axial plane aligned with said first, arcuate portion;
a third, arcuate portion extending generally rearwardly in said axial plane from said second bend, said slide having an internal, longitudinally movable pin secured thereto, said pin adapted to engage said second, straight portion when said slide is moved forward and adapted to engage said third, arcuate portion when said slide is moved rearward; and
said actuating means further comprising portions of the interior of said housing comprising:
a first abutment surface extending into the normal path of said first bend and adapted to engage same to prevent rearward motion thereof upon a predetermined amount of forward motion of said shaft.

25. An instrument according to claim 24 further comprising:
a second abutment surface extending into the normal path of said second bend and adapted to engage same to prevent forward motion thereof when said first abutment surface is in engagement with said first bend situated diametrically opposite from, and longitudinally forwardly of said first predetermined point.

26. A retractable surgical instrument comprising:
a housing;
a longitudinally movable support shaft having a proximal end thereof situated within said housing, said proximal end having a substantially planar, generally closed-loop profile in a first axial plane, said profile having at least one rearwardly projecting abutment point adapted to prevent rearward longitudinal motion of said support shaft upon engagement of said point with an abutment surface;
means for biasing said abutment point in a direction transverse to said longitudinal direction;
an operative surgical element secured to the distal end of said support shaft and movable therewith between a retracted position, wherein said surgical element is enclosed by said housing, and at least one extended position, wherein said surgical element is extended from said housing;
trigger means accessible from the exterior of said housing and longitudinally movable relative to said support shaft, said trigger means having an actuating pin projecting into said housing a predetermined distance sufficient to cause said pin to project into the plane of said substantially closed loop, said pin being movable in a second axial plane transverse to said first axial plane, whereby longitudinal motion of said pin will effect longitudinal motion of said proximal end and of said surgical element;
an abutment surface projecting into the normal path of said abutment point and automatically engaged by same upon a predetermined amount of forward longitudinal motion thereof to prevent rearward motion of said surgical element from a selected one of said extended positions.

27. An instrument according to claim 26 further comprising:
means to overcome the bias on said abutment point and to move same rearwardly to retract said surgical element.

28. A method of advancing and locking a surgical instrument having an operating element secured to a support shaft, the support shaft being reciprocally axially movable within a handle in response to manual operation of a trigger element, the method comprising the steps of advancing the operating element from the handle and locking said element relative to said handle wherein the steps of advancing an locking comprise:
moving said trigger element longitudinally forwardly a predetermined distance to extend said support shaft and operating element to a position extended from said handle;
biasing a portion of said support shaft transversely;
automatically locking said support shaft and operating element in said extended position by abutting said biased portion of said support shaft against an abutment means, this locking step being achieved only due to a predetermined amount of forward manual longitudinal motion of said trigger element.

29. A method according t o claim 28 further comprising the method of unlocking and retracting said support shaft and said surgical element into said handle, said steps of unlocking and retracting comprising:
overcoming the transverse bias of said biased portion of said support shaft to enable same to be moved rearwardly past said abutment means; and
moving said support shaft and said operating element rearwardly to retract same into said handle.

30. A method of advancing and locking, and then for unlocking and retracting a surgical instrument having an operating element secured to a support shaft, the support shaft being reciprocally axially movable within a handle in response to manual operation of a trigger element, the method comprising the steps of advancing the operating element from the handle and locking said element relative to said handle and the steps of unlocking said element and retracting same into said handle wherein the steps of advancing and locking comprise:

providing at least one abutting element on the interior of said handle for resisting rearward motion of a cooperating element;

adapting a first portion of the proximal end of said support shaft to serve as said cooperative element by abutting one of said abutting elements when placed in a predetermined position;

biasing the proximal end of said support shaft transversely relative to the axis thereof in a manner such that said abutting element is in the normal reciprocal axial path of said first portion of said proximal end;

moving said trigger element to extend said support shaft and operating element from said handle and to place said first portion of said proximal end in said predetermined position to automatically engage one of said abutting elements and said first portion of said proximal end in abutting relationship to prevent motion of said support shaft into said handle;

and wherein said steps of unlocking and retracting comprise the steps of:

engaging said trigger element with a second portion of said proximal end of said support shaft to overcome said transverse bias; and moving said trigger element axially rearwardly to retract said first portion of said proximal end of said support shaft rearwardly past said abutting element.

* * * * *